Figure 1:
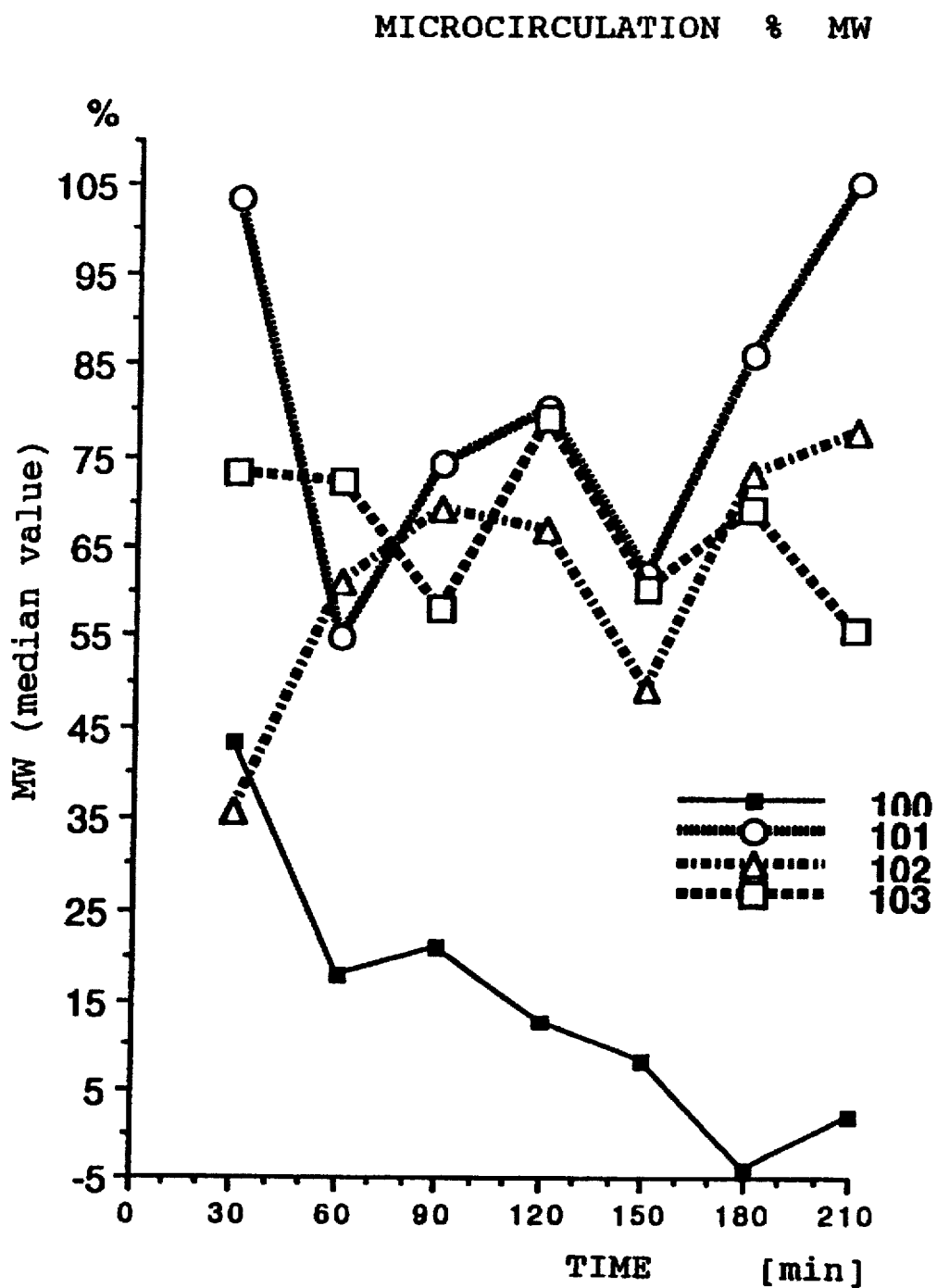

United States Patent [19]

Zastrow et al.

[11] Patent Number: 5,800,835
[45] Date of Patent: Sep. 1, 1998

[54] PREPARATION FOR IMPROVING THE BLOOD SUPPLY CONTAINING HARD MAGNETIC PARTICLES

[75] Inventors: Leonhard Zastrow, Monaco, Monaco; Dagmar Hülsenberg, Ilmenau; Karin Golz, Berlin, both of Germany; Klaus Stanzl, White Plains, N.Y.

[73] Assignee: Lancaster Group GmbH, Ludwigshafen, Germany

[21] Appl. No.: 522,304

[22] PCT Filed: Jul. 19, 1994

[86] PCT No.: PCT/DE94/00879

§ 371 Date: Sep. 5, 1995

§ 102(e) Date: Sep. 5, 1995

[87] PCT Pub. No.: WO95/03061

PCT Pub. Date: Feb. 2, 1995

[30] Foreign Application Priority Data

Jul. 19, 1993 [DE] Germany .......................... 43 25 071.8

[51] Int. Cl.$^6$ ................................................ A61K 31/715
[52] U.S. Cl. ................................... 424/647; 424/648
[58] Field of Search ................................. 424/647, 648

[56] References Cited

U.S. PATENT DOCUMENTS 5,411,730 5/1995 Kirpotin et al. .................... 424/647

FOREIGN PATENT DOCUMENTS 4108710 7/1992 Japan .

OTHER PUBLICATIONS

Beauty Forum, Feb. 1993, S. 46.
Derwent Abstracts, EP 186,616 A—86-171,075/27, J 59116214 A—84203893/33, J 59139314 A—84-2339/39, and JO 209428 A—90-110377/15.

*Primary Examiner*—James H. Reamer
*Attorney, Agent, or Firm*—Collard & Roe, P.C.

[57] ABSTRACT

The invention relates to a preparation for improving the blood supply. The problem with prior art preparations or processes resides in the fact that soft magnetic components had to be introduced into the body in capsule form or a magnetic field had to be applied after the application of demagnetized particles to the skin. The purpose of the invention is to provide a novel preparation for improving the blood supply in which special hard magnetic particles are used. According to the invention, the preparation for improving the blood supply consists of a pharmaceutically or cosmetically acceptable medium and possibly further additives containing finely distributed hard magnetic single-grade particles with a high coercitive field intensity and grain sizes in the range of 600 to 1200 nm. Dispersions of this preparation exhibit no aggregation of the hard magnetic particles. The preferred use is in the cosmetic and dermatological field.

12 Claims, 1 Drawing Sheet

PREPARATION FOR IMPROVING THE BLOOD SUPPLY CONTAINING HARD MAGNETIC PARTICLES

DESCRIPTION

The invention relates to a preparation for stimulating the circulation of blood.

Stimulation of the circulation of the skin is a problem for whose solution a number of research results have already been disclosed and for which different paths have been followed. The influence of magnetic forces has also been increasingly studied, especially in recent years.

Among other things, the use of pulsed electromagnetic fields has been studied as a potentially useful therapy for the postoperative treatment of pain and oedema (Mayrovitz, H. N., Larsen, P. B., WOUNDS, vol. 4, no. 5, 197 (1992)).

Beauty Forum 2/93, page 46, has disclosed the use of a stick which the user rubs over the skin, a magnetic field having an effect on the skin surface. According to the manufacturer, cells which are no longer fully functional are supposed to be stimulated by a magnetic field, initiating a self-healing process and restoring firmness and elasticity to the skin.

The use of magnetic polymer particles, some of which have pharmacologically active compounds coupled to them, has also been described, e.g. in U.S. Pat. No. 4,501,726, U.S. Pat. No. 4,335,094 and U.S. Pat. No. 5,039,559. In these patent descriptions, soft ferrite particles or ferroaluminates were encapsulated with polymeric materials and introduced into the body.

A magnetic cosmetic preparation is described in JP-A-4-108710 (Yoko Shiga). Here ferromagnetic substances, e.g. magnetite or manganese zinc ferrite (all soft ferrites), are dispersed in a cosmetic preparation in the demagnetized state and the preparation is magnetized after cosmetic application to the skin. This form of application is said to have a circulation-stimulating effect, namely a 3.4% increase in circulation in animal experiments with a proportion of 0.1% of magnetite. The specification contains no further information.

The object of the invention is to provide a novel preparation with a substantially improved circulation-stimulating effect. According to the invention, the preparation for stimulating the circulation contains a pharmaceutically or cosmetically acceptable excipient and optionally conventional formulation additives, in which there are finely divided, magnetically hard single-domain particles with a strong coercive field and with sizes in the range 600 to 1200 nm.

The term "single-domain particles" is understood as meaning single crystals of naturally uniform magnetic orientation. Magnetically hard single-domain particles which are particularly preferred in the present invention are barium or strontium hexaferrites, which advantageously are not doped. These undoped barium or strontium hexaferrites are prepared by known processes, e.g. by growing single crystals from a tempered glass melt in accordance with the glass crystallization technique. A suitable glass for this purpose is the three-component system $BaO—Fe_2O_3—B_2O_3$, which is advantageously composed of 20 to 50% by weight of $Fe_2O_3$, 30 to 50% by weight of BaO and 20 to 50% by weight of $B_2O_3$.

The diameter/thickness ratio of the crystals of barium hexaferrite or strontium hexaferrite is generally 3:1 to 10:1.

The sizes of the single-domain particles are preferably in the range 750 to 1000 nm and especially in the range 800 to 950 nm. In this range, the particles have a particularly advantageous, strong coercive field. The coercive field is advantageously in the range 3000 to 5000 Oersted and preferably in the range 4000 to 5000 Oersted, although it can also be higher.

The single-domain particles according to the invention can be dispersed very well in a pharmaceutically/cosmetically acceptable excipient and in additives by the conventional processes and there is only insignificant aggregation, if any, in the dispersion. This is particularly surprising because it is clear from all the publications of the state of the art that permanent-magnetic particles, i.e. magnetically hard particles, always tend to aggregate and therefore have to be incorporated into a dispersion with particular organic polymers or inorganic substances, these inorganic or organic additives functioning as a barrier substance in which the magnetically hard particles are embedded, or functioning as a result of coupling to these additives, thereby avoiding aggregation. This is not necessary in the present invention and the magnetically hard single-domain particles alone, especially the barium or strontium hexaferrites prepared by the glass crystallization technique, give a dispersion which readily produces a stable dispersion with the optional addition of certain dispersants.

The novel preparations exhibit an excellent circulation-stimulating action. With the aid of conventional cosmetic or dermatological excipients, for example, they can be processed to a composition for application to the skin, or else they can be converted to enteral or parenteral processing forms by conventional techniques and with the conventional excipient systems. When used on the skin, the redness or skin and eye irritation occurring for example with the medicinal use of conventional vasodilators are avoided, which represents an appreciable advantage in the practical application of dermatological preparations. The circulation-stimulating action also accounts for the observation of a stimulating activity on hair growth at appropriate concentrations.

The proportion of magnetically hard single-domain particles according to the invention in the dispersion is generally in the range 0.01 to 70% by weight, preferably in the range 0.01 to 15% by weight and especially in the range 0.01 to 10% by weight, based on the total weight of the dispersion.

According to the invention, it is particularly advantageous for dermal/cosmetic application if the magnetically hard single-domain particles are present in combination with asymmetric lamellar aggregates consisting of phospholipids with a phosphatidylcholine content in the range 30 to 99% by weight and oxygen-charged fluorocarbons in the range 0.2 to 100% (weight/volume), according to DE-42 21 255, to which reference is made. Here the asymmetric lamellar aggregates penetrate the skin as a function of critical solubility temperatures of the fluorocarbons or fluorocarbon mixtures used. Such a combination has an additive effect and in some cases a synergistic effect on the supply of oxygen to the skin. With the aid of the asymmetric lamellar aggregates, the magnetically hard single-domain particles are introduced in encapsulated form onto the surface of the skin and, by virtue of their magnetic force, exert a suction effect on the haemoglobin particles present in the blood, which are "pulled" into the tips of the furthest blood capillaries. This increases the supply of oxygen to the skin, which is boosted further by the oxygen brought into the skin from outside with the aid of the asymmetric lamellar aggregates.

The phospholipids used for the asymmetric lamellar aggregates are advantageously selected from the group consisting of natural phospholipids, such as soya lecithin and egg lecithin, as well as synthetic phospholipids and/or partially hydrogenated phospholipids.

It is particularly advantageous if the lipid fraction used contains very high proportions of phosphatidylcholine, especially proportions of 70 to 99% by weight. In addition to phosphatidylcholine, lysolecithin can also be present in the concentration range 1 to 10% by weight.

To achieve a slower penetration of the skin, the composition can contain fluorocarbons or fluorocarbon mixtures with a higher critical solubility temperature.

The term "fluorocarbons" used here is understood as meaning perfluorinated or highly fluorinated carbon compounds or mixtures which are capable of transporting gases such as oxygen and carbon dioxide. In terms of this invention, highly fluorinated hydrocarbon compounds are those in which most of the hydrogen atoms have been replaced with fluorine atoms, so further replacement does not necessarily increase the ability to transport gases. This is usually achieved when up to about 90% of the hydrogen atoms have been replaced with fluorine atoms. In terms of the present invention, preferred fluorine atoms are those in which at least 95% of the hydrogen atoms, preferably 98% and particularly preferably 100%, have been replaced.

A large number of fluorocarbons can be used, e.g. linear and branched aliphatic fluoroalkanes, monocyclic or bicyclic and optionally fluoroalkyl-substituted fluorocycloalkanes, perfluorinated aliphatic or bicyclic amines, bis(perfluoroalkyl)ethenes, perfluorinated polyethers or mixtures thereof. Examples of particularly preferred fluorocarbons are perfluorodecalin, F-butyltetrahydrofuran, perfluorotributylamine, perfluorooctyl bromide, bisfluoro(butyl)ethene or bisfluoro(hexyl)ethene or $C_6$-$C_9$-perfluoroalkanes.

As already stated, it is also possible to use, in addition to phosphatidylcholine, lysolecithins and/or charged phospholipids such as phosphatidylethanolamine, n-acetylphosphatidylethanolamine or phosphatidic acid, in the concentration range 0.1 to 30% by weight.

If desired, the magnetically hard single-domain particles can be coated with a layer which only slightly reduces the coercive field but prevents or inhibits the escape of barium and/or strontium ions. This can be necessary when there is a need only to use preparations from which the leaching of barium or strontium ions over a particular period of time is to be avoided as a requirement of the health authority. Examples of substances suitable for this purpose are inorganic substances such as titanium dioxide, zirconium dioxide or hydroxyapatite. Other substances can also be used, however, provided they fulfil the same function, i.e. that of keeping the escape of barium or strontium ions, by boiling with hydrochloric acid over a period of thirty minutes, below the permitted value.

The invention further relates to a process for the manufacture of the preparation. The process consists in dispersing the magnetic single-domain particles, with the optional addition of a dispersant, in a conventional excipient for pharmaceutical or cosmetic preparations, and optionally other additives, using devices with a shear action or an ultrasonic action, e.g. at speeds of rotation in the range 10,000 to 27,000 rpm higher, the size of the magnetically hard single-domain particles being in the range 600 to 1200 nm. Surprisingly, this gives a stable dispersion without the formation of aggregates normally to be expected, and thereby avoids agglomeration of the end product. This is important for cosmetic/dermatological application and necessary for parenteral administration, e.g. intravenous administration, in order to ensure a stable colloid-disperse system. The processing necessary for the latter form of administration, e.g. with polymeric substances, is avoided according to the invention.

In the case where the magnetically hard single-domain particles according to the invention are to be combined with asymmetric lamellar aggregates, the asymmetric lamellar aggregates are prepared first by the pre-emulsification of fluorocarbons in an aqueous phospholipid solution at about 12,000 to 15,000 rpm. This is followed by high-pressure homogenization with the magnetically hard single-domain particles to produce appropriate spherical lamellar structures. To avoid autoxidation processes in the unsaturated acid radical of native lipids, it is possible to add antioxidants, e.g. α-tocopherol. The fluorocarbon content and hence the oxygen availability can be varied within wide limits.

The invention further relates to the use of a pharmaceutical or cosmetic preparation for stimulating the circulation, wherein a form of administration for a pharmaceutical or cosmetic preparation, consisting of an excipient and optionally other additives, in which there are finely divided, magnetically hard single-domain particles with a strong coercive field and with sizes in the range 600 to 1200 nm, is introduced into the body or applied to the skin. The action in terms of stimulation of the circulation is determined here by the amount of single-domain particles, which penetrate the skin e.g. in the case of cosmetic/dermal use and create a corresponding magnetic field therein. Utilization of the magnetic properties of the blood for improving the blood circulation, especially in the fine capillaries, results in an improved supply of oxygen, an improved supply of nutrients and an improved removal of waste products. This leads to a remission of skin wrinkles due to old age, an improved elasticity, a rejuvenation of the skin and, in the case of cellulitis, a substantially improved clinical picture. A stimulating action on hair growth is also in evidence.

Measurements under constant physiological conditions show that an increase in the microcirculation of up to 200% could be achieved. Microcirculation is understood as meaning the circulation in the capillary region of the skin. This result proves the superiority of the preparations according to the invention compared with the previous results of the state of the art.

An additional effect can be achieved in the case of pharmaceutical preparations, e.g. dermatological preparations, by the incorporation of desired drugs. This can be carried out in conventional manner, but particularly advantageously for example by including these pharmaceutically active compounds, together with the magnetically hard single-domain particles, in the asymmetric lamellar aggregates, thereby ensuring deep penetration into the skin.

Suitable pharmaceutically active compounds are pharmacological active ingredients in the form of systemic active ingredients, including cytostatic agents, carcinostatic agents, immunomodulators and vaccines, especially those of the following group: dermatological active ingredients, for example virustatic agents or virucidal medicinal agents, antimycotic agents, heparins (e.g. heparin calcium, heparin sodium, low-molecular heparins), antibiotics, corticoids, anti-infective agents, active ingredients for acne, local anaesthetics, antiphlogistics, antihistamines or antipsoriatics; systemic active ingredients, for example non-steroidal analgesics/ antirheumatics (e.g. diclofenac sodium, diclofenac diethylamine salt, etofenamate, flufenamic acid, 2-hydroxyethyl salicylate, ibuprofen, indomethacin, piroxicam), opiate receptor agonists and antagonists (e.g. buprenorphin, fentanyl, pentazocine, pethidine, tilidine, tramadol, naloxone), histamine antagonists (e.g. bamipine lactate, chlorphenoxamine hydrochloride, clemastine hydrogenfumarate, dimethindene maleate, pheniramine hydrogenmaleate), insulins, regulatory peptides and their inhibitors (e.g. anterior pituitary hormones and their inhibitors, posterior pituitary hormones, hypothalamic hormones) or sedatives/hypnotics (e.g. diazepam); and active ingredients of the group comprising cytostatic agents, carcinostatic agents, immunomodulators and vaccines.

A preferred dermatological active ingredient is, for example rosmaric acid or another virucidal or virustatic active ingredient occurring in plants. A preferred systemic active ingredient is, for example, a low-molecular or high-molecular heparin, an oligopeptide or a polypeptide.

Other preferred active ingredients are vitamins (E, A, B, C), muramylpeptides, doxorubicin, gentamycin, gramicidin, dexamethasone, hydrocortisone, progesterone, prednisolone or derivatives thereof and/or acid or base addition salts derived therefrom, and also melanin.

With relevant active ingredients and active ingredient combinations and for appropriate indications, antineoplastic therapy and antimicrobial and antiviral therapy are possible, as are other types of therapy which, as a result of the improved oxygen supply to the skin by virtue of the preparation according to the invention, also lead to an improved absorption of the pharmaceutical active ingredients and hence are more successful.

The amounts of active ingredient in therapeutic terms are generally very small, so that, for example for the case of soluble active ingredients, solubilities of 0.5 to 12 g/100 ml are sufficient for medicinal use. If these solubilities are not attained, it is also possible to form an emulsion through the interaction of e.g. fluorocarbon and phospholipid, using known methods, in order to obtain the appropriate galenical composition. The active ingredients can therefore be incorporated into the novel excipient in the amount which is adequate in terms of current medical practice.

Excipients which can be used for the magnetically hard single-domain particles in a cosmetic preparation are the substances conventionally used for soaps, creams, lotions, emulsions, colognes, extracts, pastes, gels, powders and tinctures, it also being possible, where appropriate, for these to be in the form of a dressing, plaster or spray.

The invention will be illustrated in greater detail below by way of Examples. However, the sections of description and Examples relating to cosmetic application are not intended to imply a limitation of the invention. In the attached drawing, FIG. 1 is a graphical representation of the microcirculation with time for various test samples.

EXAMPLE 1
Preparation of a suspension with magnetically hard strontium hexaferrite powders 5 percent by weight of magnetically hard strontium hexaferrite powder in a thickness ratio of 5:1 and in the particle size range 700–1000 nm are added to a mixture of propylene glycol, glycerol and distilled water in proportions of 1:1:2 and the whole is homogenized using a Turrax homogenizer at 15,000 rpm, for a period of 30 min.

EXAMPLE 2
Preparation of a suspension with magnetically hard barium hexaferrite powders 15% by weight of magnetically hard barium hexaferrite powder in a thickness ratio of 10:1 and in the particle size range 600–800 nm are added to a mixture of propylene glycol and distilled water in proportions of 1:1 and the whole is homogenized.

| Ultrasonic disintegrator: | 400 W |
|---|---|
| Amplitude: | 50 |
| Time: | 40 min. |

EXAMPLE 3
Preparation of a suspension with magnetically hard barium hexaferrite and strontium hexaferrite powders 30% by weight of barium hexaferrite and strontium hexaferrite in proportions of 1:1 are added to a mixture of propylene glycol and distilled water in proportions of 1:1. The thickness ratios of the strontium ferrite and barium ferrite are 4:1 and 5:1 respectively. The particle size spectrum tolerates between 700 and 1000 nm.

| Homogenization parameters: | |
|---|---|
| Ultrasonic disintegrator: | 400 W |
| Amplitude: | 50 |
| Time: | 45 min. |

EXAMPLE 4.1
Preparation of liposomes with magnetically hard barium hexaferrite and strontium hexaferrite powders 0.8% by weight of magnetically hard barium hexaferrite powder in a thickness ratio of 6:1 and in the particle size range 600–800 nm is dispersed in 29% by weight of synthetic phospholipid and 1% by weight of lysolecithins.

| Turrax homogenizer: | 20,000 rpm |
|---|---|
| Time: | 7 min. |

The following substitution is possible under the same technological conditions; 0.8 percent by weight of strontium hexaferrite or a barium hexaferrite/strontium hexaferrite mixture in proportions of x% to (100−x). 10% of ethanol and gs distilled water are subsequently added.

| Turrax homogenizer: | 15,000 rpm |
|---|---|
| Time: | 20 min. |

EXAMPLE 4.2
Preparation of liposomes with magnetically hard barium hexaferrite and/or strontium hexaferrite powders 70% by weight of magnetically hard barium hexaferrite powder in a thickness ratio of 7:1 and in the particle size range 800–1000 nm are dispersed in 20% by weight of partially hydrogenated phospholipids and synthetic phospholipids in proportions of 1:1 and 10% by weight of lysolecithins.

| Ultrasonic disintegrator: | 400 W |
|---|---|
| Amplitude: | 50 |
| Time: | 30 min. |

The following substitution is possible under the same technological conditions: 70% by weight of strontium hexaferrite or a barium hexaferrite/strontium hexaferrite mixture in proportions of x% to (100–x). 10% of ethanol and qs distilled water are subsequently added.

| Ultrasonic disintegrator: | 400 W |
|---|---|
| Amplitude: | 50 |
| Time: | 70 min. |

EXAMPLE 5
Preparation of asymmetric lamellar aggregates with magnetically hard barium hexaferrite and/or strontium hexaferrite powders 0.01% by weight of magnetically hard barium hexaferrite powder in a thickness ratio of 3:1 and in the particle size range 750–900 nm is dispersed in 8% by weight of phospholipids with a phosphatidylcholine content of 30% by weight of egg lecithin.

| Turrax homogenizer: | 27,000 rpm |
|---|---|
| Time: | 5 min. |

The following substitution is possible under the same technological conditions: 0.01% by weight of strontium hexaferrite or a barium hexaferrite/strontium hexaferrite mixture in proportions of x% to (100–x). 6.0% by weight of glycerol, 6% by weight of propylene glycol, 0.2% by weight of oxygen-charged fluorocarbons and qs distilled water are subsequently added.

| Turrax homogenizer: | 25,000 rpm |
|---|---|
| Time: | 20 min. |

EXAMPLE 6
Preparation of asymmetric lamellar aggregates with magnetically hard barium hexaferrite and/or strontium hexaferrite powders 1.0% by weight of magnetically hard barium hexaferrite powder in a thickness ratio of 10:1 and in the particle size range 800–950 nm is dispersed in 10% by weight of phospholipids with a phosphatidylcholine content of 99% by weight of soya lecithin.

| Turrax homogenizer: | 27,000 rpm |
|---|---|
| Time: | 10 min. |

The following substitution is possible under the same technological conditions: 1.0 percent by weight of strontium hexaferrite or a barium hexaferrite/strontium hexaferrite mixture in proportions of x% to (100–x). 6.0% by weight of glycerol, 6% by weight of propylene glycol, 50% by weight of oxygen-charged fluorocarbons and qs distilled water are subsequently added.

| Turrax homogenizer: | 27,000 rpm |
|---|---|
| Time: | 20 min. |

EXAMPLE 7
Preparation of a fluorocarbon dispersion with magnetically hard barium hexaferrite and/or strontium hexaferrite powders 4% by weight of magnetically hard barium hexaferrite powder in a thickness ratio of 4:1 and in the particle size range 850–1000 nm are dispersed in 100% by weight of oxygen-charged fluorocarbons.

| Ultrasonic disintegrator: | 400 W |
|---|---|
| Amplitude: | 50 |
| Time: | 25 min. |

The following substitution is possible under the same technological conditions: 0.4 percent by weight of strontium hexaferrite or a barium hexaferrite/strontium hexaferrite mixture in proportions of x% to (100–x).

EXAMPLE 8
Preparation of a fluorocarbon dispersion with magnetically hard barium hexaferrite and/or strontium hexaferrite powders 60% by weight of magnetically hard strontium hexaferrite powder in a thickness ratio of 9:1 and in the particle size range 900–1200 nm are dispersed in 100 percent by weight of oxygen-charged fluorocarbons.

| Ultrasonic disintegrator: | 400 W |
|---|---|
| Amplitude: | 50 |
| Time: | 60 min. |

The following substitution is possible under the same technological conditions: 60% by weight of barium hexaferrite or a barium hexaferrite/strontium hexaferrite mixture in proportions of x% to (100–x).

EXAMPLE 9
Dermatological ointment

| Phase A: | |
|---|---|
| Beeswax | 8% |
| Synthetic lanolin | 10% |
| Phase B: | |
| Glycerol | 10% |
| Distilled H$_2$O | qs |
| Phase C: | |
| Fluorocarbon dispersion according to Example 7 | 50% |

Preparation:
Phase A is heated from 65° C., with stirring. Phase B is also heated to 65° C. and added to phase A, with stirring, the temperature remaining stable. The homogenization time is 10 minutes. This is followed by the cooling phase. When the temperature reaches ≦30° C., phase C is added, with slow stirring.

EXAMPLE 10
Dermatological paste

| Phase A: | |
|---|---|
| Cetostearyl alcohol | 5% |
| Beeswax | 15% |
| Synthetic lanolin | 20% |
| Phase B: | |
| Propylene glycol | 5% |
| Glycerol | 5% |
| Distilled H$_2$O | qs |

-continued

| Phase C: | |
|---|---|
| Fluorocarbon dispersion according to Example 6 | 30% |

Preparation:

Phase A is heated to 65° C, with stirring. Phase B is also heated to 65° C. and added to phase A, with stirring, the temperature remaining stable. The homogenization time is 10 minutes. This is followed by the cooling phase. When the temperature reaches ≦30° C., phase C is added, with slow stirring.

EXAMPLE 11
Dermatological paste

| Glycerol | 10% |
|---|---|
| Propylene glycol | 5% |
| Fluorocarbon dispersion | 85% |

The raw materials are successively mixed at room temperature.

EXAMPLE 12
Dermatological tincture

| Glycerol | 5% |
|---|---|
| Propylene glycol | 5% |
| Water | qs |
| Suspension with magnetically hard powder according to Example 1 | 1% |

All the raw materials are mixed in water, in any chosen order, at room temperature.

EXAMPLE 13
W/O emulsion

| Emulsifier system consisting of phosphoric acid ester and isopropyl palmitate in proportions of 35%:65% | 8.2% |
|---|---|
| Paraffin | 12.2% |
| Glycerol | 5.3% |
| Preservative | 0.3% |
| Water | qs |
| Dispersion with magnetically hard powder according to Example 5 | 10.0% |

Preparation in the cold: The raw materials are mixed in order and then homogenized for ca. 10 minutes.

EXAMPLE 14
O/W emulsion

| Phase A: | |
|---|---|
| Glyceryl stearate | 1.0% |
| Stearic acid | 2.0% |
| Cocoa butter | 3.0% |
| Cetyl alcohol | 1.5% |
| Oleyl alcohol | 0.5% |
| Dimethicone | 1.0% |
| Disodium EDTA | 0.15% |
| Butyl acetate/hydroxytoluene | 0.05% |

| Phase B: | |
|---|---|
| Distilled H₂O | qs |
| Carbomer | 0.5 |
| Propylene glycol | 3.5% |
| Glycerol | 2.5% |
| Preservative | 0.5% |
| Phase C | |
| TEA | 0.5% |
| Phase D | |
| Perfume oil | 0.5% |
| Dispersion with magnetically hard powder according to Example 5 | 5.0% |

Preparation: Phase A is heated to 80° C., with stirring. Phase B is also heated to 80° C.

EXAMPLE 15
Cosmetic gel

| Distilled water | qs% |
|---|---|
| Carbomer | 0.6% |
| TEA | 0.6% |
| Preservative | 0.3% |
| Propylene glycol | 3.5% |
| Glycerol | 4.0% |
| Natural oil | 2.0% |
| Perfume oil | 0.5% |
| Suspension with magnetically hard powder according to Example 2 | 2.5% |

Preparation/Preparation in the cold: The water and Carbomer are homogenized at room temperature. The remaining raw materials are added in order, with stirring.

EXAMPLE 16
Lotion

| Polyacrylic acid MW 4 million | 0.5% |
|---|---|
| Triethanolamine | 0.5% |
| Cetostearyl alcohol | 2.0% |
| Propyl glycol | 2.0% |
| Glycerol | 1.5% |
| Vitamin E | 1.0% |
| Distilled water | qs |
| Perfume oil | 0.5% |
| Preservative | 0.3% |
| Dispersion with magnetically hard powder according to Example 5 | 3.5% |

The preparation/preparation in the cold is carried out according to Example 14.

EXAMPLE 17
Hair lotion

| Distilled water | qs |
|---|---|
| Carbomer | 0.05% |
| TEA | 0.1% |
| Vitamin B | 1.0% |
| Propylene glycol | 2.0% |
| Perfume oil | 0.5% |
| Suspension with magnetically hard powder according to Example 3 | 1.5% |

The preparation/preparation in the cold is carried out according to Example 15.

EXAMPLE 18
Hair/scalp pack

| | |
|---|---|
| Distilled water | qs |
| Cetyl alcohol | 3.0% |
| Phosphoric acid ester/isopropylamide 1:1 | 6.5% |
| Coconut glycerides O | 3.5% |
| Stearic acid | 6.0% |
| Glycerol | 5.0% |
| Lecithin | 1.0% |
| Liposomes according to Example 4.1 | 20.0% |

The preparation/preparation in the cold is carried out according to Example 15.

EXAMPLE 19
O/W special emulsion
Base

| | |
|---|---|
| Phase A | |
| Cetearyl alcohol | 1.5% |
| Cetearyl alcohol and PEG-40 castor oil in proportions of 1:1 | 3.0% |
| Hexyl laurate | 1.5% |
| Dibutyl adipate | 4.0% |
| Oleyl erucate | 1.5% |
| Phase B | |
| Distilled water | qs |
| Carbomer | 0.3% |
| Allantoin | 0.2% |
| Phase C | |
| TEA | 0.3% |
| Phase D | |
| Aloe vera | 2.0% |
| Silicone oil | 3.0% |
| D-Panthenol | 0.5% |
| Babassu oil | 2.0% |
| Vitamin A palmitate | 1.0% |
| Olive oil | 2.0% |
| Preservative | 0.3% |
| Asymmetric lamellar aggregates with magnetically hard powders | 15.0% |

The preparation is carried out according to Example 14.

EXAMPLE 20

| | |
|---|---|
| Aloe vera gel | 10.0% |
| Alga gel | 5.0% |
| Ethanol | 10.0% |
| Distilled water | qs |
| Magnetic powder according to Example 1 | 55.0% |

The preparation is carried out according to Example 11.

EXAMPLE 21
Leg serum

| | |
|---|---|
| Phase A | |
| Cetearyl alcohol | 3.5% |
| Cetearyl alcohol | 1.0% |
| Phase B | |
| Carbomer | 0.5% |
| Distilled water | qs |
| Preservative | 0.3% |
| Phase C | |
| TEA | 0.5% |
| Phase D | |
| Aloe vera | 1.5% |
| Liposomes with magnetically hard powders according to Example 6 | 30.0% |

The preparation is carried out according to Example 14.

EXAMPLE 22
Shampoo

| | |
|---|---|
| Phase A | |
| Sodium lauryl-ether-sulphate | 38.0% |
| Monoethanolammonium laurylsulphate | 10.0% |
| Octamethylcyclotetrasiloxane | 5.0% |
| Jojoba oil | 0.5% |
| Distilled water | qs |
| Preservative | 0.3% |
| Fats | 0.01% |
| Perfume oil | 0.5% |
| Suspension with magnetically hard powders according to Example 2 | 3.5% |

For the preparation, the raw materials are mixed in water at room temperature.

EXAMPLE 23
Decorative powder

| | |
|---|---|
| Talc | qs |
| Kaolin | 9.5% |
| Magnesium stearate | 2.5% |
| Magnesium carbonate | 2.5% |
| Zinc stearate | 1.5% |
| Colour combination according to shade | 3.5% |
| Suspension with magnetically hard powders | 5.0% |

For the preparation, the raw materials are homogeneously mixed together in order.

EXAMPLE 24
Shower-bath cream

| | |
|---|---|
| Sodium lauryl-ether-sulphate | 35.0% |
| Glyceryl stearate and Ceteareth-20 in proportions of 1:1 | 2.0% |
| Glyceryl isostearate | 3.0% |
| Jojoba oil | 1.0% |
| Preservative | 0.3% |
| Perfume oil | 0.3% |
| Suspension with magnetically hard particles according to Example 1 | 1.5% |

For the preparation, the raw materials are mixed at room temperature.

EXAMPLE 25
Make-up fluid

| | |
|---|---|
| Emulsifier system consisting of glyceryl stearate, Ceteareth-20, Ceteareth-12, cetearyl alcohol and cetyl palmitate in approximately | 6.5% |

-continued

| equal proportions | |
|---|---|
| Glycerol | 2.5% |
| Propylene glycol | 1.5% |
| Aloe vera extract | 0.5% |
| Vitamin E | 1.0% |
| Colours | 3.5% |
| Dispersion with magnetically hard powders according to Example 7 | 10.5% |
| Water | qs |

The preparation corresponds to Example 14.

EXAMPLE 26
Lipstick

| Castor Oil | qs |
|---|---|
| Beeswax | 13.0% |
| Carnauba wax | 8.5% |
| Lanolin | 5.0% |
| Paraffin | 3.0% |
| Preservative | 0.05% |
| Pigments for imparting pearlescence | 5.0% |
| Dispersion with magnetically hard powders according to Example 8 | 1.0% |
| Colour pigments | 3.0% |

Preparation: The melt is heated to 80° C., with thorough stirring. The pigments are added at 60° C. The pouring temperature is 60° C.

EXAMPLE 27
Face mask

| Emulsifier system consisting of polyglycerol ester and stabilizers in proportions of 2:1 | 9.5% |
|---|---|
| Paraffin | 12.0% |
| Glycerol | 5.3% |
| Talc | 2.0% |
| Clay | 1.0% |
| Preservative | 0.3% |
| Distilled water | qs |
| Dispersion with magnetically hard powders according to Example 8 | 30% |

For the preparation, the raw materials are added in order, at room temperature, and homogeneously mixed.

EXAMPLE 28
Sun product

| Emulsifier system consisting of phosphoric acid ester and isopropyl palmitate in proportions of 1:1 | 10.5% |
|---|---|
| Isopropyl palmitate | 1.5% |
| Petrolatum | 5.5% |
| Paraffin | 5.0% |
| MgSO$_2$ · 7H$_2$O | 0.5% |
| Glycerol | 1.5% |
| Talc | 2.0% |
| Preservative | 0.5% |
| UV filter | 6.0% |
| TiO$_2$ | 3.0% |
| Distilled water | qs |
| Dispersion with magnetically hard powders according to Example 7 | |

For the preparation, the raw materials are added in order, at room temperature, and homogeneously mixed.

EXAMPLE 29
Pharmaceutical powder

| Talc | qs |
|---|---|
| Kaolin | 15.5% |
| Magnesium stearate | 5.0% |
| Zinc oxide | 2.0% |
| Magnesium carbonate | 2.0% |
| Suspension with magnetically hard powders according to Example 1 | 1.5% |

For the preparation, the raw materials are homogeneously mixed together in order.

EXAMPLE 30

Cosmetic preparations produced according to Example 19 were subjected to an application test in which the microcirculation of the skin was measured after the application of a sample in the form of an ointment.

The circulation of the skin is known to be obtained from the product of the blood flow and the vascular volume. In addition to vasodilation and constriction, the capillaries are subject to a pulsating vasomotion called the capillary pulse. The microcirculation was quantitatively determined using the laser Doppler flow measurement with a Periflux apparatus (Perimet KB, Sweden). The 2 mW helium-neon laser was transmitted to the measuring point through a flexible fibre-optic light guide. The optical fibre was fixed to the measuring area by means of a holder, ensuring a depth of penetration of the laser light into the skin tissue of 1.5–2 mm. A voltage was measured as the output and input signal, which, as a relative measure of the circulation of the tissue, is directly proportional to the product of the quantity of erythrocytes and the speed of the erythrocytes. The method afforded a continuous, contact-free and quantitative recording of the circulation of the skin. As the skin temperature has a large influence on the cutaneous microcirculation or on the responsiveness of the capillaries, the environmental conditions had to be approximated to those of the physiologically indifferent areas and kept constant throughout the entire duration of the experiment. These experimental conditions for test subjects were 26° C.±1 and 36%±1 relative humidity, the test subjects having already been adapted to these conditions for thirty minutes beforehand. After a blank measurement, an excess of the ointment samples was allowed to act for thirty minutes on an area of skin on the inside of the forearm. The significance level p was <0.05.

In test subjects who responded to the ointment applied, an increase in microcirculation of up to 200% was found. FIG. 1 shows an increase in microcirculation markedly above the initial value M100 for samples containing magnetically hard single-domain particles, in this case sample M101. FIG. 1 also shows the results for samples M102 and M103.

We claim:

1. A preparation for stimulating the blood circulation of the skin comprising a dispersion containing
   a proportion of finely divided magnetically hard single-domain particles in the dispersion being in the range from 0.01% to 70% by weight, based on the total weight of the dispersion; said particles having a strong coercive field and being in the range 600 to 1200 nm; and
   wherein the magnetically hard single-domain particles are selected from the group consisting of barium hexaferrite, strontium hexaferrite, undoped barium hexaferrite, undoped strontium hexaferrite, and the mixtures thereof;

wherein the magnetically hard single-domain particles are present in combination with asymmetric lamellar aggregates comprising phospholipids with a phosphatidylcholine content in the range 30% to 99% by weight and oxygen-charged fluorocarbons in the range 0.2% to 100% (weight/volume), the asymmetric lamellar aggregates penetrating the skin as a function of the critical solubility temperature of the fluorocarbons or fluorocarbon mixtures used; and the balance up to 100% by weight of a cosmetic or pharmaceutical excipient carrier substance or a pharmaceutical additive, based on the total weight of the dispersion.

2. A preparation according to claim 1, wherein the magnetically hard single-domain particles are barium hexaferrite.

3. A preparation according to claim 1, wherein the magnetically hard single-domain particles with a strong coercive field are selected from the group consisting of barium hexaferrite, strontium hexaferrite and the mixtures thereof.

4. A preparation according to claim 1, wherein the magnetically hard single-domain particles are in the range 750 to 1000 nm.

5. A preparation according to claim 1, wherein the magnetically hard single-domain particles are in the range 800 to 950 nm.

6. A preparation according to claim 1, further comprising a coating layer on the magnetically hard single-domain particles, said layer reduces the coercive field only slightly, and prevents the escape of barium ions and strontium ions.

7. A preparation according to claim 1, wherein the phospholipids are selected from the group consisting of natural phospholipids, soya lecithin, egg lecithin, synthetic phospholipids and partially hydrogenated phospholipids.

8. A preparation according to claim 1, wherein in addition to phosphatidylcholine, lysolecithins are present in the concentration range 1% to 10% by weight.

9. A preparation according to claim 1, wherein said cosmetic or pharmaceutical carrier substances or pharmaceutical additives are selected from the group consisting of cytostatic agents, carcinostatic agents, immunomodulators, vaccines, virustatic agents, virucidal medicinal agents, antimycotic agents, heparins, antibiotics, corticoids, anti-infective agents, active ingredients for acne, local anaesthetics, antiphlogistics, antihistamines, antipsoriatics, non-steroidal analgesics, non-steroidal antirheumatics, opiate receptor agonists; opiate receptor antagonists, histamine antagonists, insulins, regulatory peptides and their inhibitors, sedatives, hypnotics, rosmaric acid, a virucidal active ingredient, a virustatic active ingredient occurring in plants, oligopeptides, polypeptides, vitamin E, vitamin A, vitamin B, and vitamin C, and also the pigment melanin.

10. The preparation of claim 1, wherein the magnetically hard single-domain particles have a coercive field strength in the range of 3000 to 5000 Oersted.

11. The preparation according to claim 1, wherein said excipient is selected from the group consisting of ointment, cream, lotion, cologne, alcoholic extract, paste, gel, powder, tincture, a spray being on a dressing and a spray being on a plaster.

12. A process for the manufacture of a preparation for stimulating the blood circulation of the skin comprising incorporating magnetically hard single-domain particles with a strong coercive field and with a size in the range of 600 to 1200 nm into a pharmaceutically or cosmetically acceptable excipient or additive to form a dispersion; and wherein the magnetically hard single-domain particles are selected from the group consisting of barium hexaferrite, strontium hexaferrite, undoped barium hexaferrite, undoped strontium hexaferrite, and the mixtures thereof;

incorporating the magnetically hard single-domain particles into the excipient in combination with asymmetric lamellar aggregates consisting of phospholipids with a phosphatidylcholine content in the range of 30% to 99% by weight and oxygen-charged fluorocarbons in the range of 0.2% to 100% (weight/volume);

with the optional addition of dispersants used to form said dispersion;

wherein said dispersion contains a proportion of magnetically hard single-domain particles in the range 0.01% to 70% by weight, based on the total weight of the dispersion; and wherein the balance up to 100% by weight is said excipient or additive, based upon the total weight of said dispersion.

* * * * *